US00PP31042P3

(12) United States Plant Patent
Townsend

(10) Patent No.: US PP31,042 P3
(45) Date of Patent: Nov. 12, 2019

(54) HOP PLANT NAMED 'OR91331'

(50) Latin Name: *Humulus lupulus*
Varietal Denomination: OR91331

(71) Applicant: Oregon State University, Corvallis, OR (US)

(72) Inventor: Michael Shaun Townsend, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 15/732,802

(22) Filed: Dec. 28, 2017

(65) Prior Publication Data

US 2019/0208680 P1 Jul. 4, 2019

(51) Int. Cl.
*A01H 5/00* (2018.01)
*A01H 6/00* (2018.01)
*A01H 5/02* (2018.01)

(52) U.S. Cl.
USPC ..... Plt./236
CPC ..... *A01H 6/00* (2018.05); *A01H 5/02* (2013.01)

(58) Field of Classification Search
USPC ..... Plt./236
See application file for complete search history.

(56) References Cited

PUBLICATIONS

DeNies. Portland Monthly. Sep. 20, 2016.*
Pigg. The Daily Barometer. Nov. 6, 2017.*

* cited by examiner

*Primary Examiner* — Keith O. Robinson
(74) *Attorney, Agent, or Firm* — Klarquist Sparkman, LLP

(57) ABSTRACT

A new and distinct Hop plant cultivar named 'OR91331' is disclosed, characterized by having an early mature date, resistance to downy mildew (*Pseudoperonospora humuli* [Miyabe & Takah.] G. W. Wilson) and powdery mildew (*Podosphaera macularis* [Wallr.] U. Braun & S. Takam); vigorous with high yield potential; high alpha acids; high oil content; and high amounts of some essential oil components implicated in driving beer flavor and aroma such as myrcene, cymene, methyl heptanoate, linalool, citronellol, and terpineol.

4 Drawing Sheets

Genus and species: *Humulus lupulus*.
Variety denomination: 'OR91331'.

BACKGROUND

The present disclosure comprises a new and distinct cultivar of *Humulus lupulus*, and hereinafter referred to by the cultivar name 'OR91331'.

The new hop plant resulted from a planned breeding program from crossing *Humulus lupulus* 'Perle' (unpatented), as the female parent and an unknown male parent (as the female plants were open pollinated). The resulting hop plant was selected when growing in a cultivated area in Corvallis, Oreg. in 2010.

SUMMARY

During October, 2009, open pollinated seed was collected from a 'Perle' hop yard growing near Corvallis, Oreg. This seed was stratified at 34° F. for 8 weeks, and planted into flats containing a standard soil mix in a greenhouse in Corvallis, Oreg. in January 2010. Established hop seedlings were screened for powdery mildew resistance and general vigor. Selected plants were transplanted into a field nursery under a 6 foot tall trellis near Corvallis, Oreg. in May, 2010. These plants were given one string for climbing support, and were evaluated for general vigor, sex, and downy and powdery mildew resistance during the 2010 growing season.

During January 2011, plants selected after short trellis screening were transplanted while dormant to a spaced-plant nursery under a standard 18 foot trellis near Corvallis, Oreg. 'OR91331' was one of the plants selected and transplanted to the standard trellis. 'OR91331' was rated for downy mildew and powdery mildew in 2011, 2012, 2013, and 2014, and due to sporadic infestation at the Corvallis site, hop aphid and hop looper damage in 2012 and 2014. 'OR91331' was successfully propagated from rhizome and stem cuttings during February 2013 in a greenhouse in Corvallis, Oreg., and transplanted into a replicated nursery on two Willamette Valley, Oreg. commercial hop farms during June, 2013 along with 3 other experimental hop genotypes. One farm was located near Silverton, Oreg., the other farm was located near Independence, Oreg. Each nursery contained 4 blocks, and each plot within a block contained 5 plants. These advanced testing nurseries were managed by the grower using the same techniques that they used for managing their commercial hop yards. Disease and pest data were not collected from the advanced testing plots due to the growers aggressively treating these nurseries to minimize disease and pest infestations.

Beginning in September 2012, 'OR91331' entered sensory testing via small, organized groups of craft brewers in the Western Oregon region. Brewers assessed the dry-rub aroma characteristics, followed by assessing the hop's flavor and aroma profile when dosed into a basic pale ale that was brewed without hops but bittered with iso-alpha extract.

During September 2013, several craft brewers began pilot brewing trials with 'OR91331' that was harvested from advanced plots near Silverton and Independence, Oreg. 'OR91331' was propagated and established in a 3 acre experimental block near Silverton Oreg., and a 7.5 acre experimental block near Independence, Oreg. during July, 2015. These experimental blocks were each managed by a commercial hop grower using their normal hop production practices. These experimental blocks were harvested in 2016 and 2017, processed by a Portland, Oreg. hop merchant, and used for test brewing.

The 'OR91331' variety is distinguished from other hop plant varieties due to the following unique combination of characteristics. When grown in Oregon's Willamette Valley, 'OR91331' is:

1. early maturing;
2. resistant to downy and powdery mildew (*Pseudoperonospora humuli* [Miyabe & Takah.] G. W. Wilson);
3. is vigorous with high yield potential;
4. has high alpha acids;
5. has high oil content; and
6. has high amounts of some essential oil components implicated in driving beer flavor and aroma such as myrcene, cymene, methyl heptanoate, linalool, citronellol, and terpineol.

Asexual reproduction of the new cultivar 'OR91331' was first performed in Corvallis, Oreg. via rhizomes. Subsequent propagations have been via rhizomes and stem cuttings. This genotype has been stable for four successive propagations.

DETAILED BOTANICAL DESCRIPTION

Figure 1:
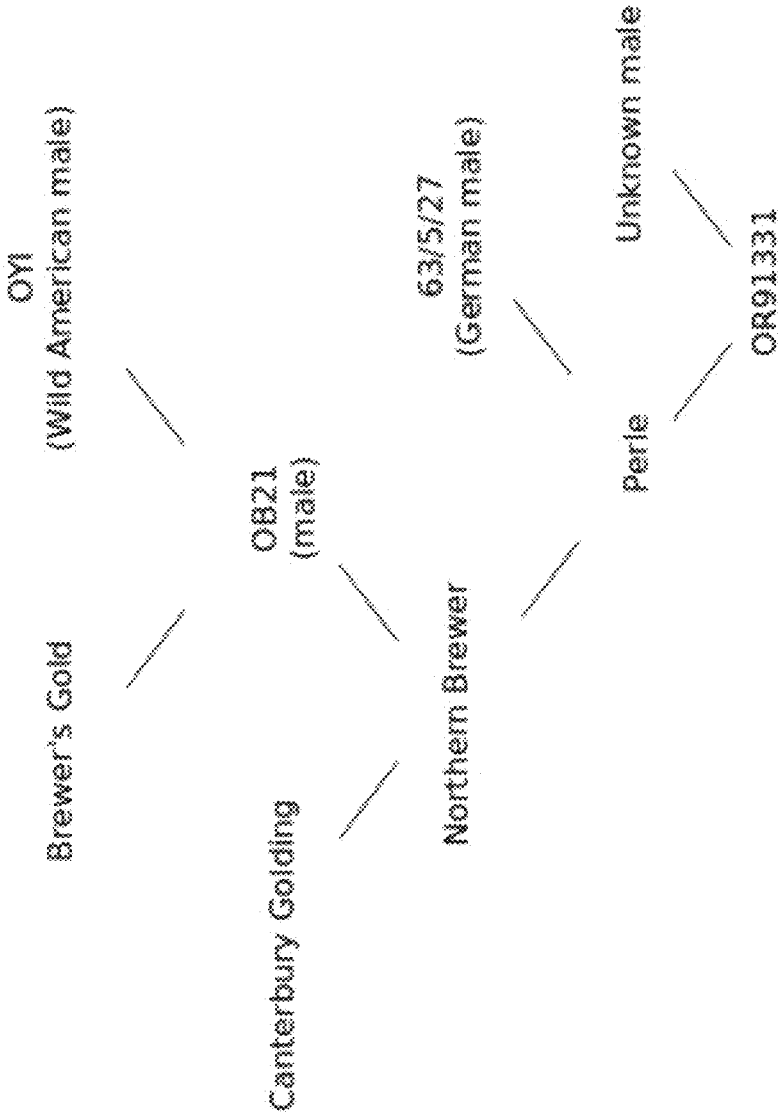
FIG. 1 illustrates the pedigree for 'OR91331'.
Figure 2:
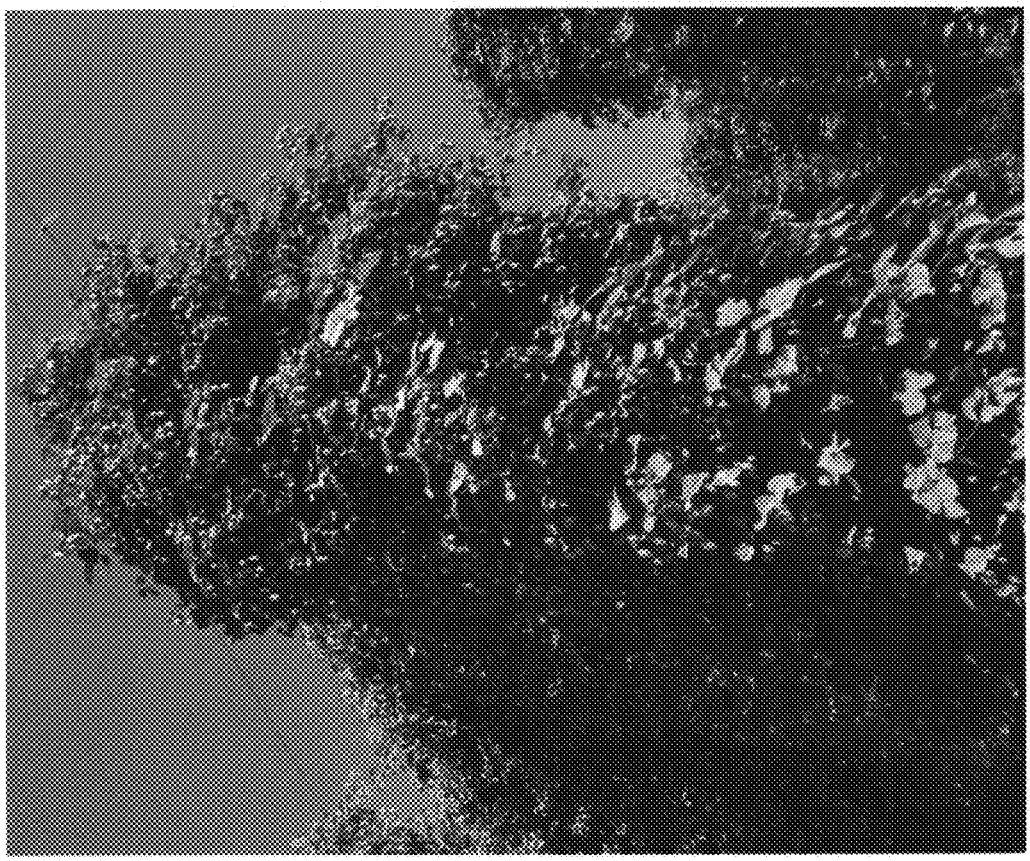
FIG. 2 shows a 3-year old, 3rd propagation generation of 'OR91331' growing near Silverton, Oreg. in August, 2017.
Figure 3:
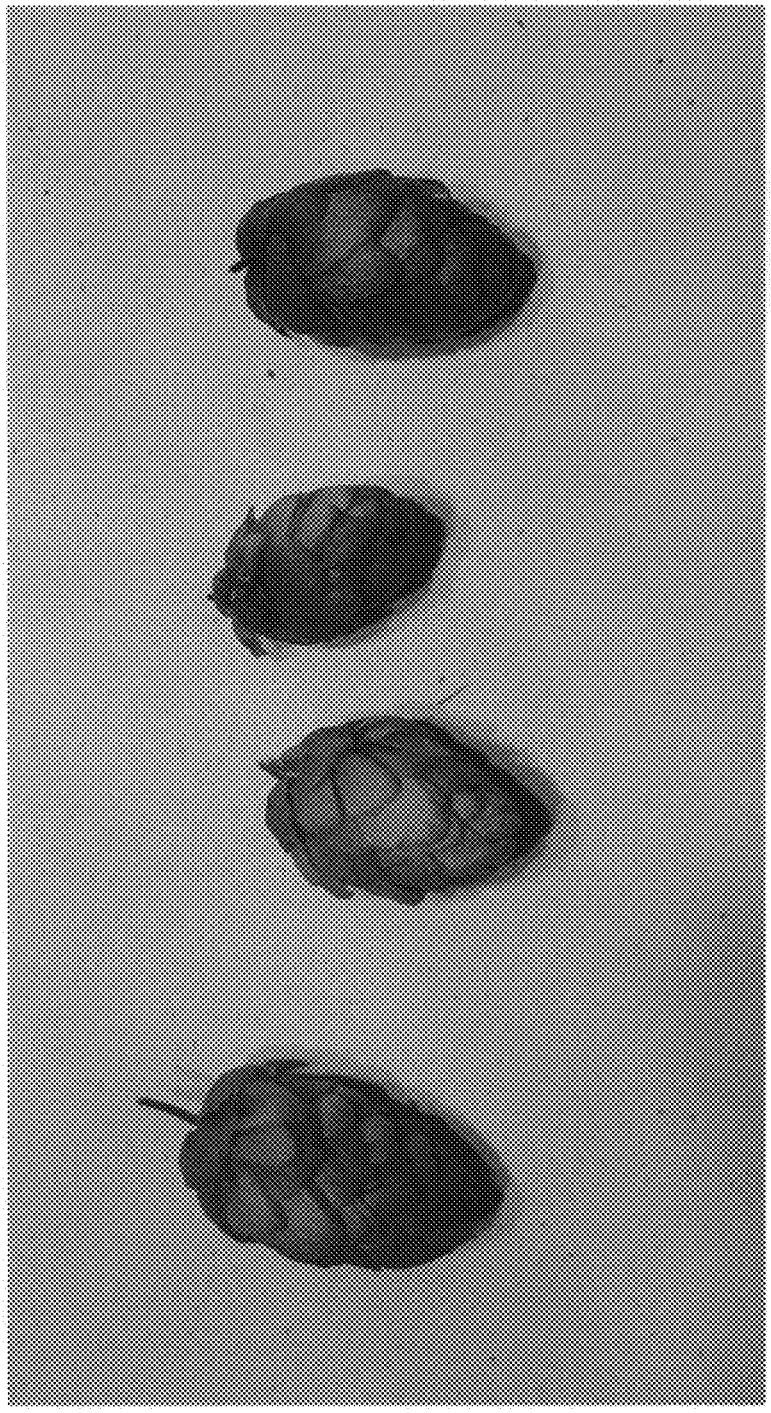
FIG. 3 shows mature cones of 'OR91331' from a 3-year old plant growing near Silverton, Oreg. in August 2017.
Figure 4:
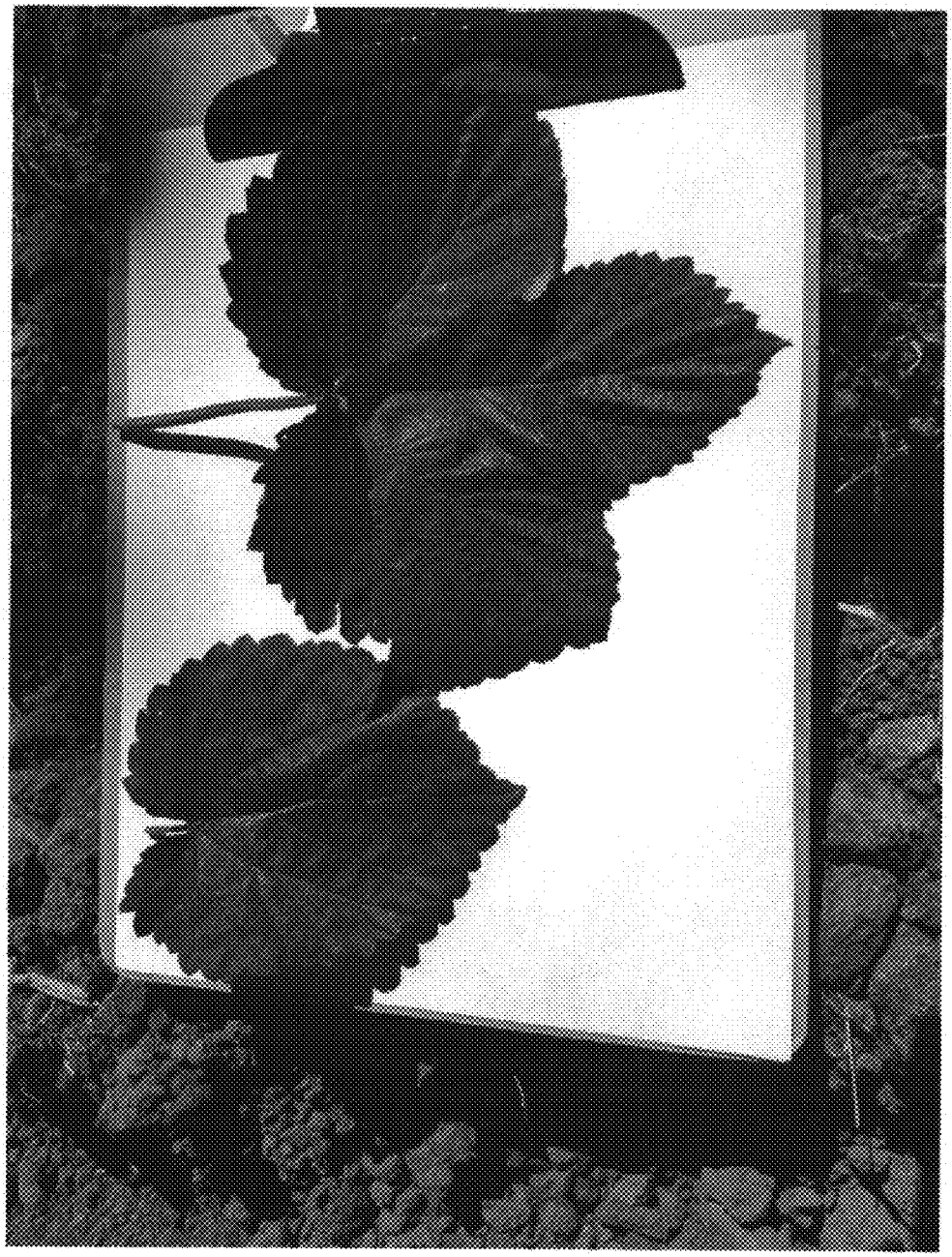
FIG. 4 shows mature leaf examples for a 3rd propagation generation, 3-year old mature 'OR91331' plant growing near Silverton, Oreg. in August, 2017.

The following detailed description of the 'OR91331' variety is based on observations of a 3-year old plant, 3rd propagation generation, growing on a commercial farm near Silverton, Oreg. in August, 2017. The original plant and progeny have been observed growing in a cultivated area near Silverton, Oreg. The new cultivar has not been evaluated under all possible environmental conditions. Certain characteristics of this variety, such as growth and color, may change with changing environmental conditions (e.g., light, temperature, moisture, nutrient availability, or other factors). The color descriptions are all based on *The Royal Horticultural Society Colour Chart, 5th* edition, 2007.

Parentage:

*Female parent.—Humulus lupulus* 'Perle'.

*Male parent.*—Unknown.

Comparison to 'Cascade': The female parent for 'OR91331' is the German aroma hop 'Perle'. The male parent is unknown as 'OR91331' arose from an open-pollinated seed. The closest known commercial hop genotype to 'OR91331' is 'Cascade'. The hop variety 'OR91331' differs from 'Cascade' in notable ways when grown in Oregon's Willamette Valley, it's target environment: 1. 'OR91331' matures 5-7days earlier than 'Cascade'. 2. 'OR91331' is resistant to powdery mildew (*Podosphaera macularis* [Wallr.] U. Braun & S. Takam), 'Cascade' is susceptible to race 6 of this pathogen. 3. 'OR91331' has shorter cone than 'Cascade'. 4. Hop cone chemistry is sensitive to several non-genetic factors including harvest timing, post-harvest processing, and disease and pest pressure. Given these factors, 'OR91331' typically contains higher amounts of the following chemical components than 'Cascade': alpha acids, total essential oil, alpha pinene, myrcene, cymene, methyl heptanoate, citronellal, linalool, caryophyllene, terpin-4-ol, humulene, alpha terpineol, and citronellol. 'OR91331' typically contains less farnesene, citral 2, nerol, damascenone, and ionone than 'Cascade'. Data is provided below in Table 1.

TABLE 1

| | 'OR91331' | 'Perle' | 'Cascade' |
|---|---|---|---|
| Alpha acids | 13.17 ± 0.89 | 7.70 ± 2.85 | 7.48 ± 0.94 |
| | *11.68-14.64* | *4.05-11.63* | *6.19-8.63* |
| Beta acids | 5.89 ± 0.52 | 3.25 ± 0.64 | 6.71 ± 0.98 |
| | *5.08-6.89* | *2.47-4.14* | *5.16-7.49* |
| Cohumulone | 0.213 ± 0.016 | 0.24 ± 0.03 | 0.31 ± 0.09 |
| | *0.17-0.24* | *0.19-0.29* | *0.14-0.41* |
| Colupulone | 0.479 ± 0.029 | 0.46 ± 0.04 | 0.50 ± 0.09 |
| | *0.44-0.53* | *0.36-0.52* | *0.33-0.57* |
| Oil | 2.48 ± 0.43 | 1.64 ± 0.62 | 1.92 ± 0.47 |
| | *2.0-3.2* | *1.0-2.7* | *1.1-2.4* |
| Alpha Pinene | 2.40 ± 0.84 | 1.47 ± 0.86 | 1.88 ± 0.03 |
| | *1.42-4.73* | *0.52-2.88* | *1.85-1.91* |
| Beta Pinene | 20.19 ± 8.13 | 7.41 ± 7.42 | 16.95 ± 1.51 |
| | *10.88-39.47* | *0.01-27.15* | *14.64-18.31* |
| Isobutyle Isobutyrate | 4.43 ± 2.76 | 5.40 ± 8.73 | 1.93 ± 0.20 |
| | *1.47-11.18* | *1.92-28.52* | *1.69-2.21* |
| Myrcene | 1527.92 ± 594.19 | 839.78 ± 418.75 | 1084.57 ± 312.45 |
| | *451.97-3002.26* | *359.80-1651.73* | *556.16-1302.33* |
| Limonene | 6.59 ± 3.56 | 5.59 ± 2.75 | 4.56 ± 0.39 |
| | *3.13-17.09* | *1.36-11.81* | *3.88-4.83* |
| Cymene | 4.02 ± 6.07 | 4.03 ± 5.87 | 0.15 ± 0.09 |
| | *0.18-22.51* | *0.04-18.99* | *0-0.23* |
| Methyl Heptanoate | 10.64 ± 11.80 | 5.18 ± 6.70 | 2.20 ± 1.26 |
| | *0-49.18* | *0-21.99* | *0-3.05* |
| Hexenol | 0.24 ± 0.10 | 0.18 ± 0.05 | 0.18 ± 0.11 |
| | *0-0.43* | *0.12-0.24* | *0-0.26* |
| Citronellal | 2.67 ± 1.13 | 2.24 ± 1.82 | 1.28 ± 1.19 |
| | *1.50-5.16* | *0.40-4.40* | *0.61-3.4* |
| Linalool | 21.59 ± 7.97 | 9.69 ± 5.23 | 9.01 ± 1.20 |
| | *12.38-38.70* | *3.96-25.74* | *7.13-10.37* |
| Caryophyllene | 170.65 ± 164.00 | 206.68 ± 139.77 | 38.28 ± 46.61 |
| | *0-485.04* | *24.86-393.80* | *14.02-121.55* |
| Terpin-4-ol | 121.86 ± 104.54 | 38.61 ± 45.88 | 76.56 ± 44.01 |
| | *0-245.23* | *0-90.99* | *0-107.76* |
| Farnesene | 2.31 ± 3.27 | 43.58 ± 43.62 | 122.62 ± 11.23 |
| | *0-9.62* | *0-141.09* | *109.16-136.11* |
| Humulene | 696.08 ± 167.38 | 583.72 ± 296.46 | 253.81 ± 19.74 |
| | *441.05-1109.40* | *2221.84-1124.63* | *222.68-277.42* |
| Citral 1 | 2.62 ± 5.63 | 9.19 ± 12.90 | 1.94 ± 4.33 |
| | *0-17.28* | *0-30.48* | *0-9.69* |
| Citral 2 | 0.46 ± 0.44 | 3.31 ± 4.21 | 3.26 ± 2.24 |
| | *0-1.74* | *0.16-10.32* | *1.03-6.29* |
| Alpha Terpineol | 16.39 ± 15.34 | 0.70 ± 0.96 | 7.38 ± 4.18 |
| | *0.77-39.88* | *0-3.12* | *0-9.76* |
| Geranyl Acetate | 11.21 ± 22.87 | 1.08 ± 1.04 | 8.72 ± 9.20 |
| | *0-66.30* | *0.12-3.85* | *3.73-25.16* |
| Citronellol | 40.88 ± 22.11 | 16.69 ± 23.72 | 20.68 ± 2.41 |
| | *0-61.82* | *0-55.00* | *17.56-23.50* |
| Nerol | 7.40 ± 2.81 | 7.69 ± 6.34 | 10.96 ± 6.07 |
| | *0.6-12.9* | *0.94-17.47* | *3.06-19.39* |
| Damascenone | 0.49 ± 0.36 | 0.88 ± 1.15 | 7.24 ± 7.78 |
| | *0-1.11* | *0-2.77* | *0-15.84* |
| Geraniol | 3.11 ± 2.05 | 3.74 ± 3.53 | 2.896 ± 0.82 |
| | *1.20-9.46* | *0.69-9.76* | *2.04-4.25* |
| Ionone | 0.21 ± 0.09 | 0.19 ± 0.05 | 0.43 ± 0.45 |
| | *0-0.37* | *0.12-0.24* | *0-0.97* |
| Caryophyllene Oxide | 3.44 ± 4.80 | 5.16 ± 5.62 | 1.26 ± 0.75 |
| | *0.17-16.96* | *0.67 ± 19.24* | *0-1.96* |

TABLE 1-continued

| | 'OR91331' | 'Perle' | 'Cascade' |
|---|---|---|---|
| Epoxides | 4.61 ± 5.68<br>*0.65-18.30* | 9.96 ± 9.98<br>*1.47-35.73* | 2.79 ± 1.65<br>*0-4.31* |

Chemical attributes for 'OR91331', 'Perle', and 'Cascade' when grown in Oregon's Willamette Valley.
Top row is mean ± standard deviation on top, bottom row in italics is the range.
Data are normalized to 8% cone dry matter and the units are mg compound per 100 gm dried hop tissue.

Ploidy: Diploid.

Plant: Vigorous climbing bine.

*Shape.*—Columnar.

*Plant head volume.*—Medium.

Bine:

*Color.*—Mature plant bine is light green (RHS 145A) with occasional red striping (RHS 180A) on the bine margin.

*Anthocyanin coloration.*—Absent.

*Internode length* (*cm*).—Average=24.0, range=17.4-27.8.

*Diameter* (*cm*).—Average=0.77, range=0.7-1.0.

*Length* (*ft*).—18-21.

Petiole:

*Length.*—Average=14.2, range=8.7-17.7.

*Color.*—Green (RHS 141D) with some red (RHS 180A) shading.

*Shape.*—Flat upper surface with channel.

Leaf:

*Arrangement.*—Opposite.

*Shape.*—Cordate to 3-lobed.

*Color.*—Upper surface: Dark green (RHS 137D); lower surface: green (RHS N138B).

*Mature leaf width* (*cm*).—Average=18.5, range 11.8-22.7.

*Mature leaf length* (*cm*).—Average=19.9, range=13.3-24.7.

*Main bine leaf lobing.*—Primarily 3-lobed with occasional cordate.

*Vein color.*—Light green (RHS 149C).

*Blistering.*—Absent.

*Leaf margin.*—Serrated.

*Lateral length, mid-canopy* (*cm*).—Average=91.9, range=28.3-129.5.

*Lateral internode length, 2nd internode from main bine* (*cm*).—Average=19.0, range=12.4-25.7.

Cone:

*Flowering date.—July* 15-20.

*Length* (*cm*).—Average=2.98, range=2.4-3.7.

*Width* (*cm*).—Average=1.79, range=1.3-2.1.

*Number of bracts per cone.*—Average=18.6, range=16-25.

*Number of bracteoles per cone.*—Average=34.2, range=28-41.

*Total bracts+bracteoles per cone.*—Average=52.8, range 44-64.

*Bract length* (*cm*).—Average=1.56, range=1.3-1.9.

*Bract width* (*cm*).—Average=1.05, range=0.8-1.3.

*Bract apex.*—Typically 1-2 mm.

*Bract color.*—Yellowish green (RHS 141D).

*Bracteole length* (*cm*).—Average=1.52, range=1.3-1.7.

*Bracteole width* (*cm*).—Average=0.91, range=0.7-1.1.

*Bracteole color.*—Yellowish green (RHS 141D). Comparative cone data is provided in Table 2.

TABLE 2

Cone architecture measurements for four hop genotypes grown near Silverton, Oregon in 2017. Data are in centimeters.

| | Cone | | Bract | | Bracteole | |
|---|---|---|---|---|---|---|
| | Length | Width | Length | Width | Length | Width |
| 9-1-331 | 2.98 b | 1.79 | 1.56 b | 1.05 | 1.52 b | 0.91 a |
| 'Perle' | 2.91 b | 1.75 | 1.35 c | 0.93 | 1.39 c | 0.70 b |
| 'Cascade' | 3.67 a | 1.90 | 1.67 b | 1.01 | 1.55 b | 0.87 a |
| 'East Kent Golding' (unpatented) | 3.87 a | 1.82 | 1.82 a | 1.02 | 1.81 a | 0.84 a |
| LSD (0.05) | 0.37 | NS | 0.14 | NS | 0.13 | 0.12 |

Agronomic traits:

*Commercial yield.*—1800-2100 lbs/ac (dried) (2 commercial farms, 2 harvests at each).

*Harvest date.*—Typically ripened between August 21-September 1 in Oregon's Willamette Valley. Typical harvest is August 25, approximately 7 days before 'Cascade' and 'Perle'.

Pathogen resistance:

*Downy mildew* (*Pseudoperonospora humuli* [*Miyabe & Takah.*] *G. W. Wilson*).—Resistant, symptoms have not been observed in 8 years of testing at 3 Willamette Valley locations.

*Powdery mildew.*—Resistant, symptoms have not been observed in 8 years of testing at 3 Willamette Valley locations.

*Verticillium wilt* (*Verticillium albo-atrum Reinke & Berthier*)&(*Verticillium dahliae Kleb*).—Unknown.

*Hop looper* (*Hypnea humuli Harris*).—Tolerant, 3.5 on a 0-5 scale where 0 is no damage, 5 is severe damage.

*Damson hop aphid* (*Phorodon humuli Schrank*).—Moderately resistant, 1 on a 0-4 scale where 0 is no aphids present, 4 is severe infestation.

Sensory observations: Sensory assessment was initiated in September 2012, and to date, approximately 100 different brewers representing 11 different breweries have participated in dry-rub and hop tea evaluations of 'OR91331'. General dry rub characters described are notes of soft rounded fruits such as melons and tropical fruits combined with notes from sharper, tangy fruits such as berries and citrus. Herbal notes similar to *Cannabis* have also been reported. When 'OR91331' is used on the "hot side" of the brewing process, brewers report fresh tropical, citrus, and berry notes in beer such as passion fruit, grapefruit, strawberry, and sauvignon blanc wine grape. When 'OR91331' is used on the "cold side" of the brewing process such as when dry-hopping, notes that are emphasized include grapefruit and *Cannabis* aromas.

I claim:

1. A new and distinct cultivar of hop plant, substantially as herein shown and described.

* * * * *